(12) United States Patent
May et al.

(10) Patent No.: US 10,285,740 B2
(45) Date of Patent: May 14, 2019

(54) SURGICAL INSTRUMENT AND METHOD

(71) Applicant: Warsaw Orthopedic, Inc., Warsaw, IN (US)

(72) Inventors: Jason M. May, Cordova, TN (US); William A. Rezach, Atoka, TN (US); Rodney R. Ballard, Lakeland, TN (US)

(73) Assignee: Warsaw Orthpedic, Inc., Warsaw, k, IN (US)

( * ) Notice: Subject to any disclaimer, the term of this patent is extended or adjusted under 35 U.S.C. 154(b) by 315 days.

(21) Appl. No.: 14/645,232

(22) Filed: Mar. 11, 2015

(65) Prior Publication Data
US 2016/0262809 A1   Sep. 15, 2016

(51) Int. Cl.
*A61B 17/70* (2006.01)
*A61B 17/16* (2006.01)

(52) U.S. Cl.
CPC ...... *A61B 17/7082* (2013.01); *A61B 17/1637* (2013.01)

(58) Field of Classification Search
CPC ........ A61B 17/7074–17/7092; A61B 17/8875; A61B 17/8886; A61B 17/8891
See application file for complete search history.

(56) References Cited

U.S. PATENT DOCUMENTS

| | | | | |
|---|---|---|---|---|
| 2,370,407 | A * | 2/1945 | McCartney | B25B 23/10 81/453 |
| 4,438,769 | A * | 3/1984 | Pratt | A61B 17/0642 227/147 |
| 4,570,624 | A * | 2/1986 | Wu | A61B 17/1728 606/96 |
| 4,763,548 | A * | 8/1988 | Leibinger | A61B 17/8891 81/453 |
| 4,887,020 | A * | 12/1989 | Graham | H02K 19/26 310/183 |
| 5,649,931 | A * | 7/1997 | Bryant | A61B 17/8891 606/104 |
| 5,667,513 | A * | 9/1997 | Torrie | A61B 17/0401 606/104 |
| 6,189,422 | B1 * | 2/2001 | Stihl | A61B 17/8891 81/452 |
| 6,860,889 | B2 * | 3/2005 | Bonati | A61B 17/8891 606/104 |
| 7,090,680 | B2 * | 8/2006 | Bonati | A61B 17/92 606/104 |
| 2002/0020255 | A1 * | 2/2002 | Simon | A61B 17/8891 81/453 |

* cited by examiner

*Primary Examiner* — Ellen C Hammond
*Assistant Examiner* — Tessa M Matthews (57) ABSTRACT

A surgical instrument having a first member engageable with a first end of a fastener having a second end configured to penetrate tissue. A second member includes an expandable member configured for engaging the first end. Systems and methods are disclosed.

20 Claims, 9 Drawing Sheets

SURGICAL INSTRUMENT AND METHOD

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to the exterior of two or more vertebral members. This disclosure describes an improvement over these prior art technologies.

SUMMARY

In one embodiment, a surgical instrument is provided. A surgical instrument includes a first member engageable with a first end of a fastener having a second end configured to penetrate tissue. A second member includes an expandable member configured for engaging the first end. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system are discussed in terms of medical devices for the treatment of musculoskeletal disorders and more particularly, in terms of a surgical system and a method for treating a spine. In some embodiments, the system comprises a surgical instrument and related methods of use, which can be employed with spinal constructs including bone fasteners and connectors having a pop on, snap on, click on and/or slide on member that provides a universal connection system to spine surgeons. In some embodiments, the spinal construct allows the use of a singular bone screw component with multiple types of receivers thereby minimizing inventory while creating assemblies customized for a specific patient.

In some embodiments, the system comprises a surgical instrument and related methods of use, which can be employed with bone screw shanks that are not pre-coupled to a tulip head. In some embodiments, such bone screws without pre-coupled tulip heads allow for modular implant selection with minimal inventory in an operating room and an ability to provide a spinal rod receiver attachment in-situ.

In one embodiment, the system includes a surgical instrument, such as, for example, a bone screw driver configured to drive a bone screw shank without a tulip head. In one embodiment, the system includes a driver configured to provide a secure engagement to a bone screw that does not have a traditional tulip head or other type of spinal rod receiver member. In one embodiment, the system includes a driver having an inner sleeve with a flexible collet. In one embodiment, the system includes a driver having a flexible collet configured to snap around a spherical head of the bone screw by pushing an outer sleeve down that is configured to force the inner sleeve down. In one embodiment, the system includes a driver having inner and outer sleeves coupled together with a threaded interface and are configured for relative translation from a first open position to a second closed position.

In one embodiment, the system includes a driver having an outer sleeve configured to prevent a flexible collet from expanding in a closed position and allows disengagement from the bone screw in an open position. In one embodiment, the system includes a driver having an outer sleeve that is configured to apply a force to a retaining cap of a driver shaft as the outer sleeve is translated. In one embodiment, the system includes a driver having an outer sleeve configured for translation to apply a compression force between a bone screw and a collet to secure the screw to the driver thereby reducing toggle between the bone screw and the driver shaft.

In one embodiment, the system includes a driver having a tip that simulates a shape of a tulip head and provides a hard stop preventing the bone screw from threading too far. In one embodiment, the system includes a driver having a tip that is a reamer configured to bore a path to allow a tulip head to be engaged without interference from a patient anatomy.

In one embodiment, the system includes a surgical instrument, such as, for example, a driver. In some embodiments, the driver has an outer sleeve having an outer sleeve tube. In some embodiments, the outer sleeve has a handle configured to rotate relative to the outer sleeve tube. In some embodiments, the driver has an inner sleeve and a driver shaft with an orientation pin. In some embodiments, the driver has a retainer cap. In one embodiment, the system includes a driver having a threaded handle configured to translate an outer sleeve and apply a compression force between a bone screw and an inner sleeve. In one embodiment, the system includes a driver having a reamer tip. In one embodiment, the system includes a driver having a collet on an inner sleeve configured to snap onto a sphere of a bone screw.

In one embodiment, the system includes a driver having a tip configured to simulate a tulip head and prevent a bone screw from being driven too deep into a patient anatomy to allow a tulip head attachment. In one embodiment, the driver has a collet on the inner sleeve.

In one embodiment, the system includes a driver that provides a secure and rigid connection between a bone screw without a tulip head or receiver component. In one embodiment, the system includes a driver that facilitates the use of implant systems in which a tulip head can be attached to the bone screw.

In one embodiment, the system includes an instrument having a collar that slides over a spherical head of a fastener. In one embodiment, the system includes an instrument having three sleeves. In one embodiment, the system includes an instrument having an internal shaft configured as a driver. In one embodiment, the system includes an instrument having a combination of two sleeves disposed around an outside of a driver. In one embodiment, the instrument includes a driver configured to extend beyond a sleeve such that an end of the driver extends past an end of the sleeve to the fastener. In one embodiment, the system includes an instrument having a sleeve configured to translate over a top of the fastener and rotated along a threaded engagement with a second sleeve for locking the instrument. In one embodiment, the system includes an instrument configured to prevent the fastener from penetrating too deep into tissue to allow an implant to be connected with the head of the fastener. In one embodiment, the system includes an instrument having an end tip of a sleeve configured to replicate a geometry of a fastener receiver to facilitate connection of the fastener receiver with the head of the fastener. In one embodiment, the system includes an instrument having a diameter at an end of an outer sleeve similar to a diameter of a tulip receiver for a fastener.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics.

In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-9, there are illustrated components of a surgical implant system 10, in accordance with the principles of the present disclosure.

The components of system 10 can be fabricated from biologically acceptable materials suitable for medical applications, including metals, synthetic polymers, ceramics and bone material and/or their composites. For example, the components of system 10, individually or collectively, can be fabricated from materials such as stainless steel alloys, aluminum, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10, which includes surgical instrument 12, is employed, for example, with an open or mini-open, minimal access and/or minimally invasive including percutaneous surgical technique to deliver and fasten an implant at a surgical site within a body of a patient, for example, a section of a spine. In one embodiment, the components of system 10 are configured to fix a bone fastener with tissue for a surgical treatment to treat various spine pathologies, such as those described herein.

Figure 1:
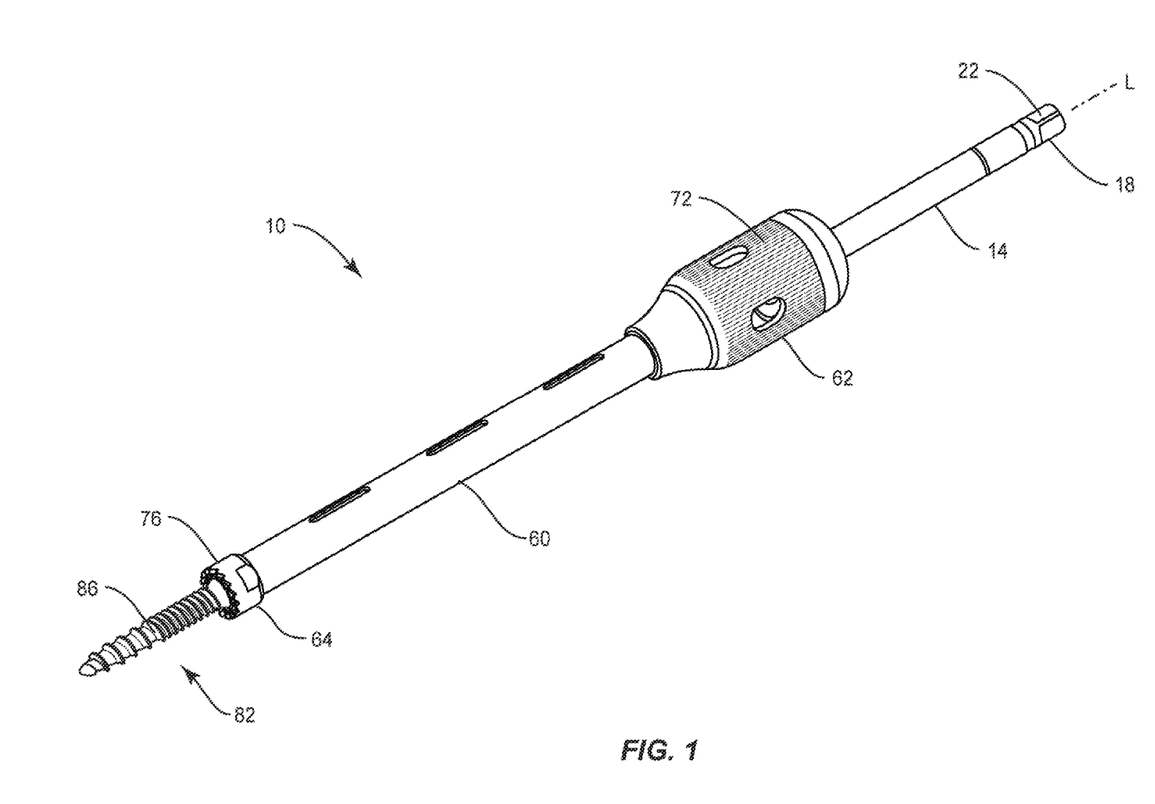
FIG. 1 is a perspective view of components of one embodiment of a surgical system in accordance with the principles of the present disclosure.
Figures 2, 3:
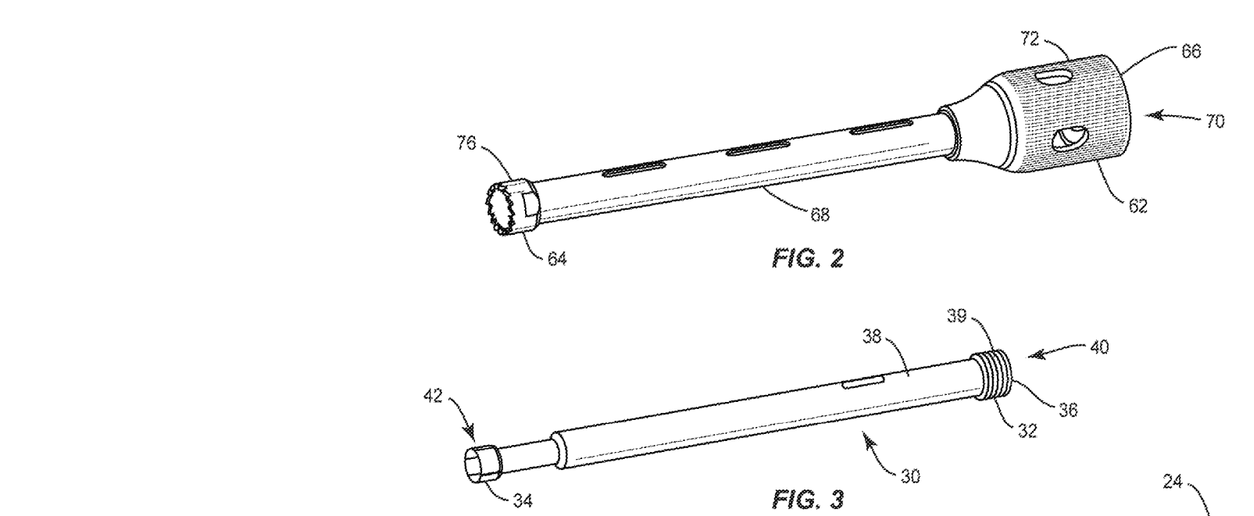
FIG. 2 is a perspective view of the components shown in FIG. 1.
FIG. 3 is a perspective view of the components shown in FIG. 1.
Figure 4:
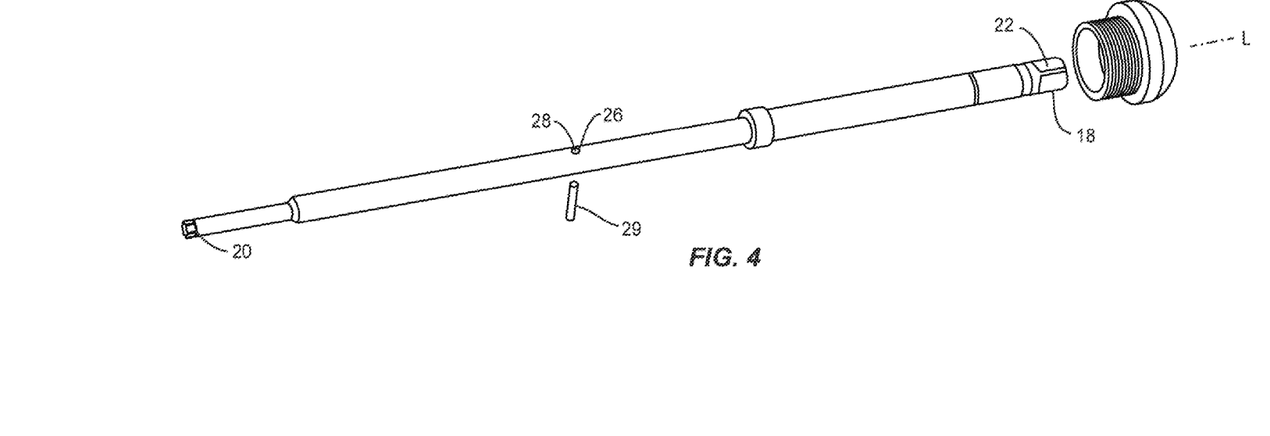
FIG. 4 is a perspective view of the components shown in FIG. 1.
Figure 4A:
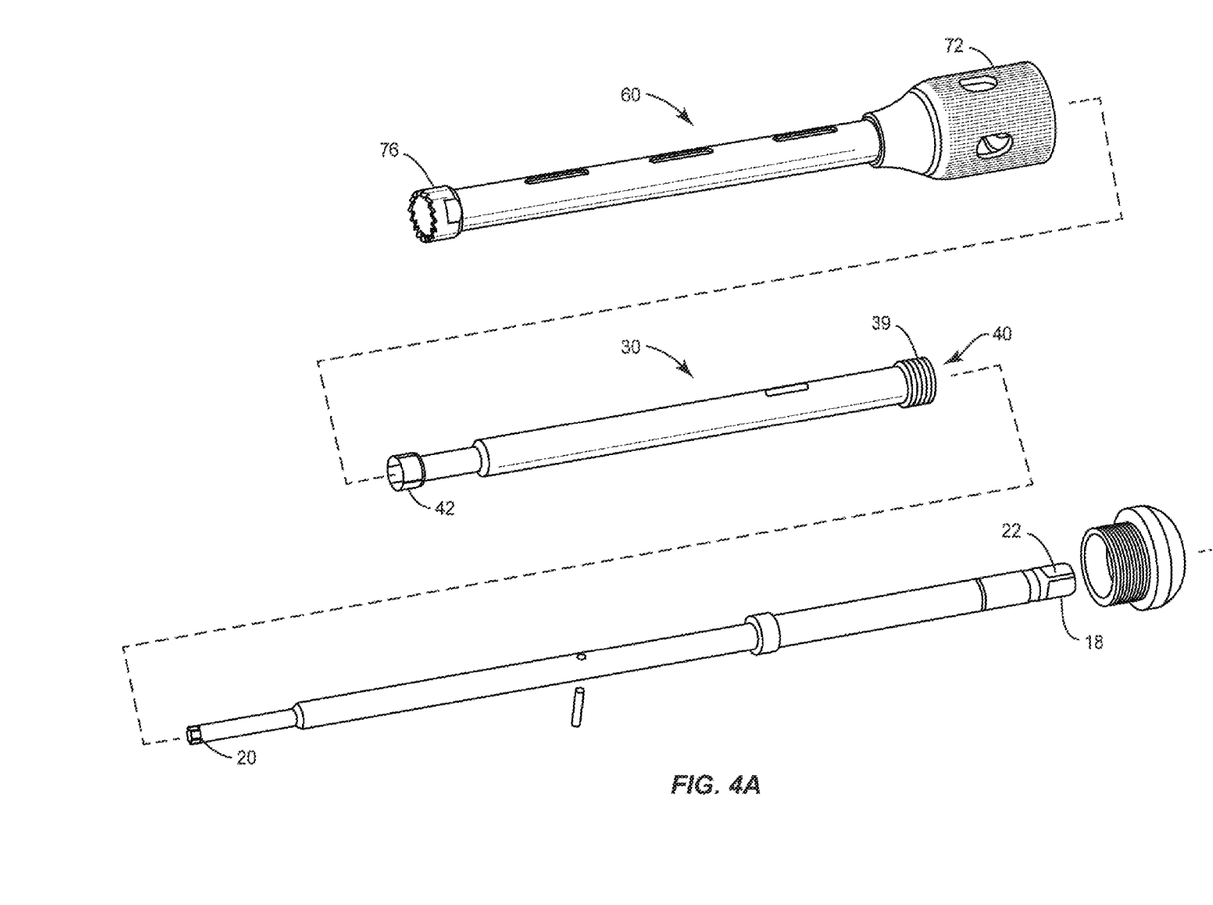
FIG. 4a is a break away view of the components shown in FIG. 1.
Figure 5:
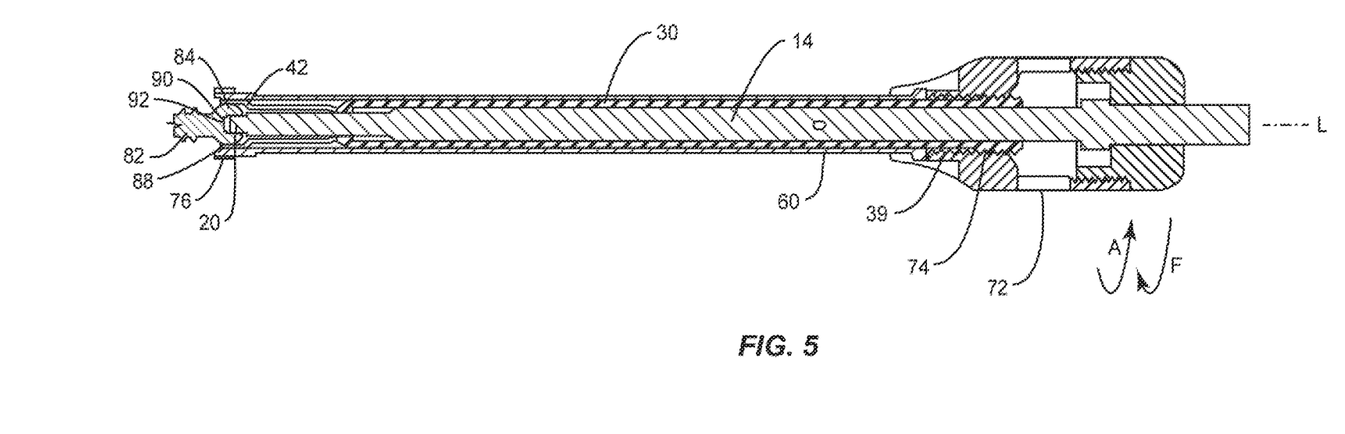
FIG. 5 is a cross-section view of the components shown in FIG. 1.
Figure 6:
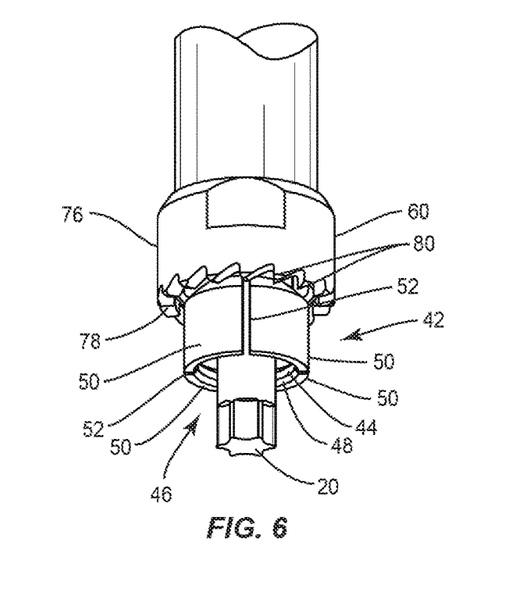
FIG. 6 is a break away view of components shown in FIG. 1.
Figure 7:
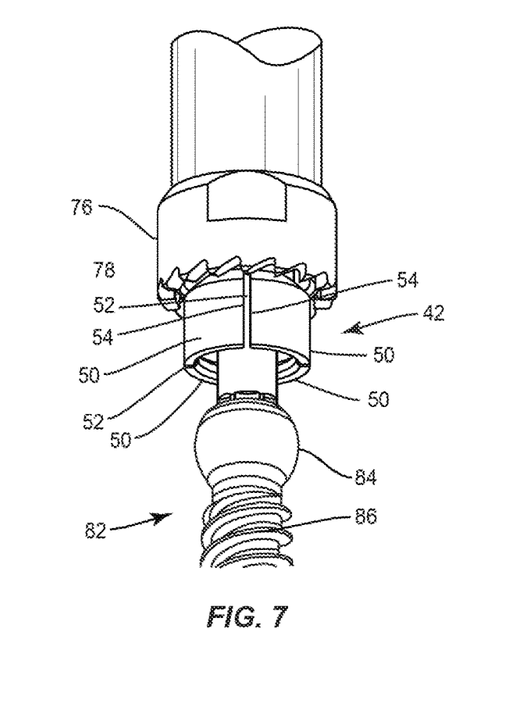
FIG. 7 is a break away view of components shown in FIG. 1.
Figure 8:
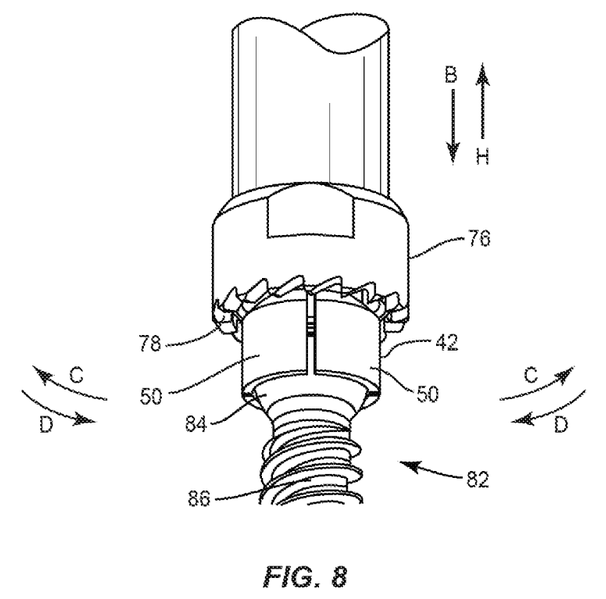
FIG. 8 is a break away view of components shown in FIG. 1.
Figure 9:
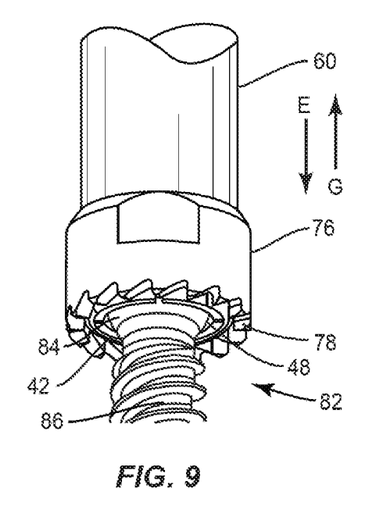
FIG. 9 is a break away view of components shown in FIG. 1.

System 10 includes surgical instrument 12, which includes a member, such as, for example, a driver shaft 14 extending along an axis L between an end 18 and an opposite end 20, as shown in FIGS. 4-5. End 18 includes a mating surface 22 configured to facilitate manipulation and/or maneuvering of surgical instrument 12. Surface 22 is configured for engagement with a retaining cap 24. In one embodiment, driver shaft 14 includes a surface 26 that defines a cavity 28 configured to receive an orientation pin 29.

End 20 is configured for engagement with an implant, such as, for example, a bone fastener 82, as shown in FIG. 5. In some embodiments, end 20 may have different cross-sections such as square, hexagonal, polygonal, triangular, star or hexalobe. End 20 may have various surface configurations, such as, for example, smooth, rough, arcuate, undulating, porous, semi-porous, dimpled, polished and/or textured.

A member, such as for example, a sleeve 30 is configured for disposal of driver shaft 14. Sleeve 30 extends between an end 32 and an end 34 along axis L. Sleeve 30 includes an inner surface 36 and an outer surface 38. Surface 36 defines a passageway 40 coaxial with axis L and configured for disposal of driver shaft 14. Surface 38 includes a threaded portion 39 configured for engagement with a third member, as described herein. End 34 includes an expandable member, such as, for example, a collet 42.

Collet 42 extends from end 34 and is configured for movement between a first configuration and a second configuration, as described herein. Collet 42 comprises an inner surface 44 defining a passageway 46, as shown in FIGS. 6-9. Passageway 46 is coaxial with passageway 40. Passageway 46 has a cylindrical cross-section configuration. In some embodiments, passageway 46 may have various cross section configurations, such as, for example, oval, oblong, triangular, rectangular, square, polygonal, irregular, uniform, non-uniform, variable, tubular and/or tapered.

Collet 42 includes a locking surface 48 defined by a plurality of cantilevered fingers 50 extending radially outward. Fingers 50 are circumferentially disposed and are equidistantly spaced apart. Fingers 50 are spaced apart by a gap 52 defined by opposite planar sidewalls 54. In one embodiment, collet 42 is flexible such that collet 42 is biased in the first, dosed position, as described herein. Collet 42 is configured to snap fit around a first end, such as, for example, a head 84 of fastener 82. As collet 42 translates over head 84 of fastener 82, collet 42 moves from a first dosed position to a second open position and back to the first closed position to capture head 84.

System 10 includes a third member, such as, for example, a sleeve 60. Sleeve 60 extends between an end 62 and an end 64 along axis L. Sleeve 60 includes an inner surface 66 and an outer surface 68. Surface 66 defines a passageway 70 coaxial with axis L and configured for moveable disposal of sleeve 30. In one embodiment, inner surface 66 may have various surface configurations to enhance engagement of sleeve 30 and/or collet 42, such as, for example, rough, arcuate, undulating, porous, semi-porous, dimpled, polished and/or textured.

End 62 includes a handle 72 having a threaded inner surface 74 configured to rotatably engage threaded portion 39 for axial translation of sleeve 60 relative to sleeve 30, which causes releasable locking of collet 42 with bone fastener 82, as discussed herein. End 64 includes a tip 76 defining a reamer end surface 78. Reamer end surface 78 includes a plurality of teeth 80 configured to bore a path around head 84.

Sleeve 60 is configured to lock collet 42 with head 84, as discussed herein, for releasable fixation with bone fastener 82. Sleeve 60 extends along a portion of sleeve 30 and is configured for axial translation relative to sleeve 30. As sleeve 60 axially translates, in the direction shown in by arrow E in FIG. 9, fingers 50 are driven further inwardly by the force of sleeve 60 engaging collet 42 such that fingers 50 are moveable to the locked position around head 84 with locking surface 48.

System 10 includes a fastener, such as, for example, a bone fastener 82. Fastener 82 includes a head 84 configured for engagement with driver shaft 14 and an elongated shaft 86 configured for penetrating tissue. Head 84 comprises a spherical configuration. Head 84 includes an outer circumferential surface 88 having a substantially uniform diameter thereabout. In some embodiments, all or only a portion of surface 88 includes a spherical configuration. Head 84 includes an inner surface 90 that defines a cavity, such as, for example, a mating surface 92. Mating surface 92 is configured for disposal of an instrument and/or tool extension, such as, for example, end 20 of driver shaft 14, as discussed herein. Mating surface 92 is centrally positioned with respect to head 84. Mating surface 92 is coaxial with axis L. In some embodiments, mating surface 92 may have various cross-section configurations, such as, for example, oval, oblong, triangular, rectangular, square, polygonal, irregular, uniform, non-uniform, variable, tubular and/or tapered. In some embodiments, inner surface 90 may have various surface configurations, such as, for example, smooth and/or surface configurations to enhance engagement with the mating surface of driver shaft 14, such as, for example, rough, arcuate, undulating, porous, semi-porous, dimpled, polished and/or textured.

Shaft 86 has a cylindrical cross section configuration and includes an outer surface having an external thread form. In some embodiments, the thread form may include a single thread turn or a plurality of discrete threads. In some embodiments, other engaging structures may be disposed on shaft 86, such as, for example, a nail configuration, barbs, expanding elements, raised elements and/or spikes to facilitate engagement of shaft 86 with tissue, such as, for example, vertebrae.

In some embodiments, all or only a portion of shaft 86 may have alternate cross section configurations, such as, for example, oval, oblong, triangular, square, polygonal, irregular, uniform, non-uniform, offset, staggered, undulating, arcuate, variable and/or tapered. In some embodiments, the outer surface may include one or a plurality of openings. In some embodiments, all or only a portion of the outer surface may have alternate surface configurations to enhance fixation with tissue such as, for example, rough, arcuate, undulating, mesh, porous, semi-porous, dimpled and/or textured. In some embodiments, all or only a portion of shaft 86 may be disposed at alternate orientations, relative to a longitudinal axis of bone fastener 82, such as, for example, transverse, perpendicular and/or other angular orientations such as acute or obtuse, co-axial and/or may be offset or staggered. In some embodiments, all or only a portion of shaft 86 may be cannulated.

In assembly, operation and use, a surgical implant system 10, similar to the systems and methods described herein, is employed with a surgical procedure for treatment of a spinal disorder affecting a section of a spine of a patient, as discussed herein. For example, system 10 can be used with a surgical procedure for treatment of a condition or injury of an affected section of the spine including vertebrae. In some embodiments, one or all of the components of system 10 can be delivered as a pre-assembled device or can be assembled in situ. System 10 may be completely or partially revised, removed or replaced.

For example, system 10 can be employed with a surgical treatment of an applicable condition or injury of an affected section of a spinal column and adjacent areas within a body, such as, for example, vertebrae (not shown). In some embodiments, system 10 may be employed with one or a plurality of vertebra. To treat a selected section of the vertebrae, a medical practitioner obtains access to a surgical site including the vertebrae in any appropriate manner, such as through incision and retraction of tissues. In some embodiments, system 10 can be used in any existing surgical method or technique including open surgery, mini-open surgery, minimally invasive surgery including percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of implantable components of system 10. A preparation instrument (not shown) can be employed to prepare tissue surfaces of vertebrae, as well as for aspiration and irrigation of a surgical region.

Surgical instrument 12 is disposable in a first position such that collet 42 is in a biased closed position extending a distance from end 64 of sleeve 60. End 20 of driver shaft 14 is engaged with mating surface 92. Rotation of handle 72, in the direction shown by arrow A in FIG. 5, causes sleeve 30 to translate along axis L, in the direction shown by arrow B in FIG. 8, to cause collet 42 to capture head 84. Fingers 50 of collet 42 expand, in the direction shown by arrow C in FIG. 8, into a second position as fingers 50 translate over surface 88. As fingers 50 translate over surface 88, fingers 50 are urged due to the resilient bias of fingers 50 into the first position, by moving in the direction shown by arrow D in FIG. 8, to snap fit around head 84 to capture head 84 within fingers 50. Locking surface 48 is in contact with surface 88. Further rotation of handle 72 causes sleeve 60 to translate, in the direction shown by arrow E in FIG. 9, such that end 76 of sleeve 60 translates over collet 42 and compresses fingers 50 of collet 42 and tighten fingers 50 about surface 88 of head 84 to releasably fix surgical instrument 12 with fastener 82.

Translation of sleeve 60 causes teeth 80 of reamer end surface 78 to bore into tissue disposed about head 85. In some embodiments, reamer end surface 78 creates a circumferential pathway around head 84 providing space for an implant, such as, for example, a spinal rod receiver to be connected with head 84.

Driver shaft 14 is rotated to apply a torsional force to bone screw 82 and increase the depth of the pilot hole and/or fasten bone screw 82 with tissue. As the depth of the pilot hole increases, shaft 86 engages the outer layer of cortical bone such that further rotation of bone screw 82 about axis L causes shaft 86 to move through the pilot hole and the outer layer of cortical bone and into a layer of cancellous bone. In some embodiments, bone screw 82 is rotated until the shaft of bone screw 82 penetrates the vertebra to fix bone screw 82 with the tissue.

The components of system 10, including surgical instrument 12 and bone screw 82, are employed to augment one or more surgical treatments. Surgical instrument 12 is disposable in the first, non-locking orientation, as described herein, to release bone screw 182 from collet 60. To disengage instrument 12 from fastener 82, handle 72 is rotated in the opposite direction, shown by arrow F in FIG. 5, to translate sleeve 60, in the direction shown by arrow G, to release the compression force about collet 42. Rotation of handle 72 causes sleeve 30 to translate, in the direction shown by arrow H in FIG. 8, to translate fingers 50 away from head 84 to disengage fingers 50 from head 84. End 20 of driver shaft 14 is disengaged from mating surface 92.

Surgical instrument 12 may be re-assembled for use in a surgical procedure. In some embodiments, system 10 may comprise various instruments including a lock and collet configuration of the present disclosure, with, for example, inserters, extenders, reducers, spreaders, distractors, blades, retractors, clamps, forceps, elevators and drills, which may be alternately sized and dimensioned, and arranged as a kit.

Upon completion of a procedure, surgical instrument 12, surgical instruments and/or tools, assemblies and non-implanted components of system 10 are removed and the incision(s) are closed. One or more of the components of system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 10. In some embodiments, system 10 may include one or a plurality of plates, connectors and/or bone fasteners for use with a single vertebral level or a plurality of vertebral levels.

In one embodiment, as shown in FIGS. 10-15, spinal implant system 10, similar to the systems and methods described herein, comprises instrument 12 described herein, having driver shaft 14, sleeve 30 and a sleeve 160, similar to sleeve 60, described herein. Driver shaft 14 extends along an axis L between an end 18 and an opposite end 20.

Figure 10:
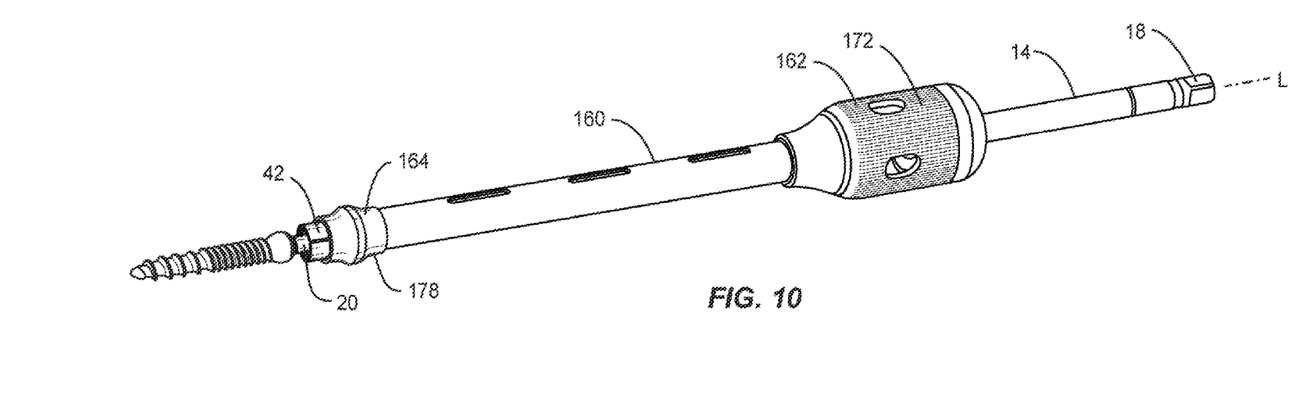
FIG. 10 is a perspective view of components of one embodiment of a surgical system in accordance with the principles of the present disclosure.
Figure 11:
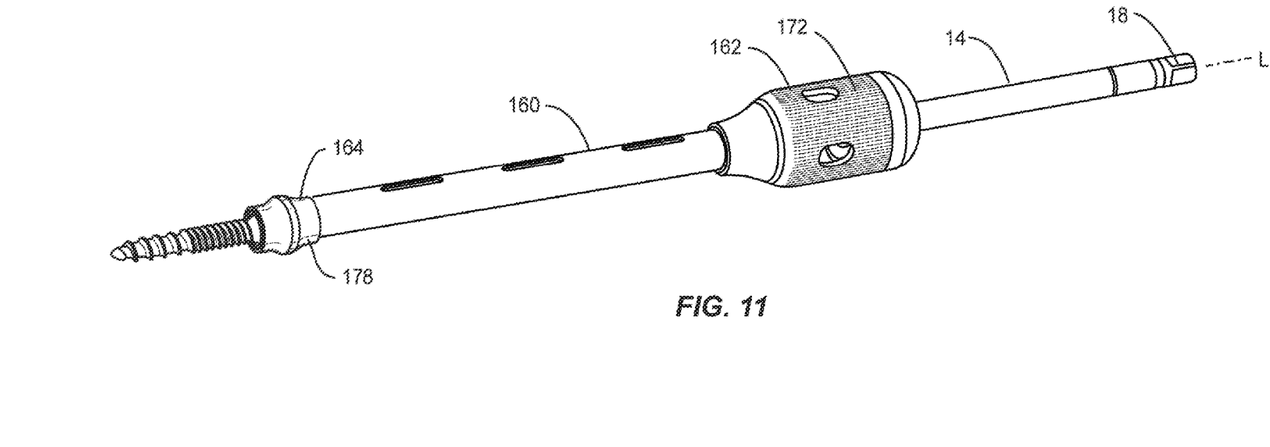
FIG. 11 is a perspective view of the components shown in FIG. 10.
Figure 12:
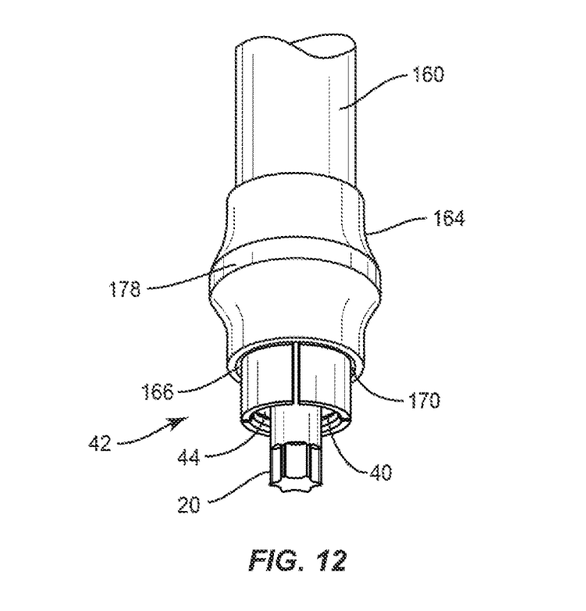
FIG. 12 is a break away view of components shown in FIG. 10.
Figure 13:
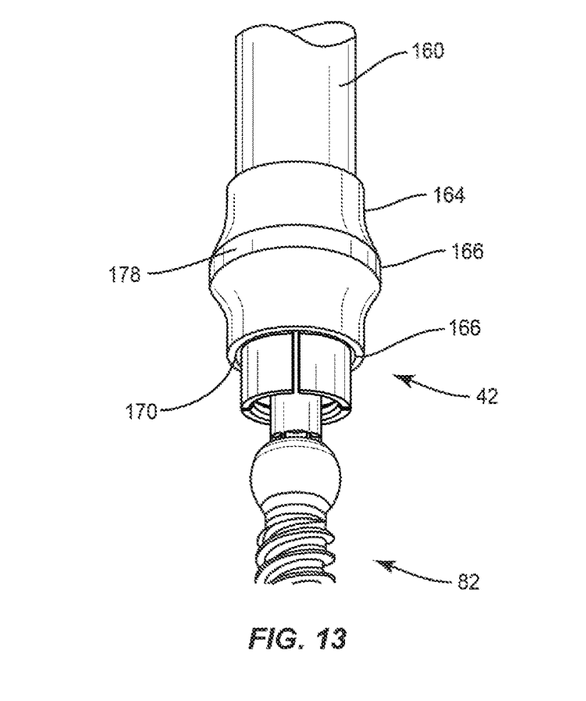
FIG. 13 is a break away view of components shown in FIG. 10.
Figure 14:
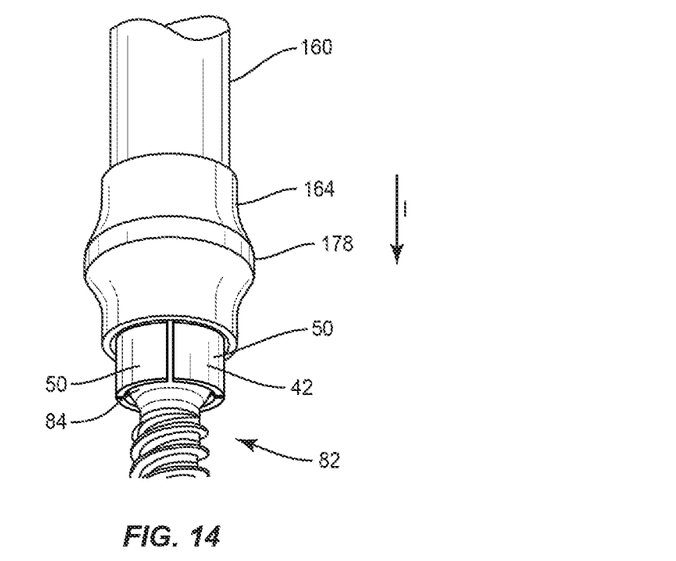
FIG. 14 is a break away view of components shown in FIG. 10.
Figure 15:
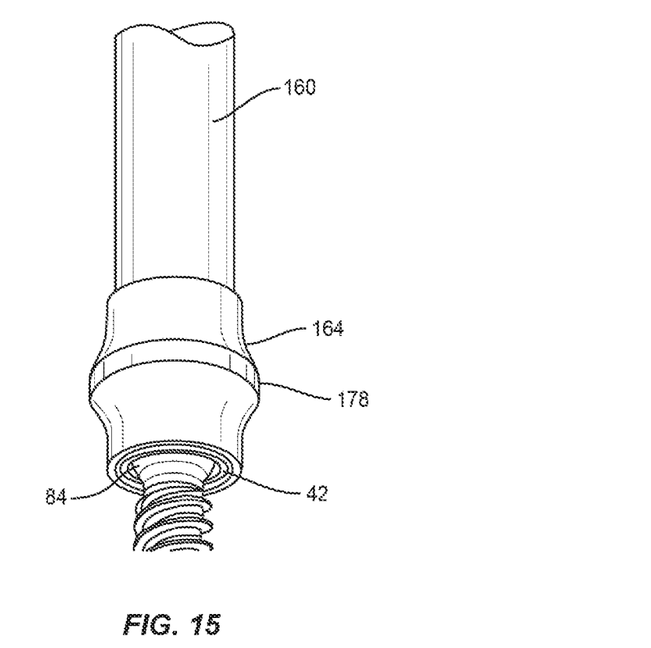
FIG. 15 is an end view of components of the surgical system shown in FIG. 10.

End 20 is configured for engagement with bone fastener 82, as shown in FIG. 10. Sleeve 30 is configured for disposal of driver shaft 14. Sleeve 30 extends along axis L. Sleeve 30 includes a passageway 40 coaxial with axis L and configured for disposal of driver shaft 14. Sleeve 30 includes collet 42, as described herein. Collet 42 is configured for movement between a first configuration and a second configuration, as described herein. Collet 42 comprises an inner surface 44 defining a passageway 46, as shown in FIGS. 12-13. Passageway 46 is coaxial with passageway 40.

Sleeve 160 extends between an end 162 and an end 164 along axis L. Sleeve 160 includes an inner surface 166 and an outer surface 168. Surface 166 defines a passageway 170 coaxial with axis L and configured for moveable disposal of sleeve 30.

End 162 includes a handle 172 having a threaded inner surface (not shown), similar to threaded surface 74. The threaded surface is configured to rotatably engage threaded portion 39 for axial translation of sleeve 160 relative to sleeve 30, which causes releasable locking of collet 42 with bone fastener 82, as discussed herein. End 164 is dimensioned and/or configured similar to a tulip head receiver, as shown in FIG. 12. End 164 includes a diameter similar to a diameter of a tulip head receiver. End 164 defines a cavity configured to receive collet 42 and head 84 such that end 164 is disposed about head 84 and collet 42 such that there is space disposed about head 84 for connection of a receiver.

Sleeve 160 is configured to lock collet 42 with head 84, as discussed herein, for releasable fixation with bone fastener 82. Sleeve 160 extends along a portion of sleeve 30 and is configured for axial translation relative to sleeve 30. As sleeve 60 axially translates, in the direction shown by arrow I in FIG. 14, fingers 50 are driven inwardly by the force of sleeve 160 engaging collet 42 such that fingers 50 are moveable to the locked position about head 84 with locking surface 48.

End 164 includes a hard stop portion 178 configured to prevent fastener 82 from penetrating into tissue beyond a selected limit. Hard stop portion 178 allows for connection of a receiver with head 84.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member defining a longitudinal axis, the first member being engageable with a first end of a fastener having a second end configured to penetrate tissue;
   a second member including a threaded portion and an expandable member configured for engaging the first end, the expandable member comprising a collet that is movable between a first, closed position and a second, open position, the collet being biased to the first, closed position;
   a third member having a threaded inner surface directly engaging the threaded portion to translate the third member relative to the second member; and
   a pin that extends through the first member and into the second member to prevent the first member from rotating relative to the second member in opposite directions about the longitudinal axis.

2. A surgical instrument as recited in claim 1, further comprising the fastener, wherein the first end includes a spherical shape.

3. A surgical instrument as recited in claim 1, further comprising the fastener, wherein the collet is configured to snap around the first end.

4. A surgical instrument as recited in claim 1, wherein the third member is configured to move the collet between the first, closed position and the second, open position.

5. A surgical instrument as recited in claim 1 further including a retaining cap configured to apply a force to form a compression fit between the first end and the second member.

6. A surgical instrument as recited in claim 1, further comprising the fastener, wherein the third member has a tip defining a cavity for disposal of the first end, the third member including a hard stop configured to prevent the fastener from penetrating into tissue beyond a selected limit.

7. A surgical instrument as recited in claim 1, wherein the third member has a tip defining a reamer end surface configured to bore a path about the first end.

8. A surgical instrument as recited in claim 7, wherein the reamer end surface includes a plurality of teeth.

9. A surgical instrument as recited in claim 1, wherein the collet is engageable by the third member to lock the collet in the first, closed position.

10. A surgical instrument as recited in claim 1, further comprising the fastener, wherein the collet moves from the first, closed position to the second, open position and then back to the first, closed position as the collet translates over the first end.

11. A surgical instrument as recited in claim 1, wherein the third member includes a passageway, the second member being movably positioned within the passageway to move between a first configuration in which the collet is spaced apart from the passageway and a second configuration in which the collet is positioned within the passageway.

12. A surgical system comprising:
a fastener comprising a first end including a socket and a second end configured to penetrate tissue;
a first member extending along a longitudinal axis between a first end that is disposed within the socket and an opposite second end that includes a mating surface;
a second member defining a first passageway having the first member disposed therein, the second member extending between a first end and a second end that includes a threaded portion, the first end of the second member comprising a collet that engages the first end of the fastener;
a pin that extends through a cavity of the first member and into a slot of the second member to prevent the first member from rotating relative to the second member in opposite directions about the longitudinal axis; and
a third member defining a second passageway having the second member disposed therein, the third member extending between a first end that includes a reamer end surface and a second end that includes an inner thread that engages the threaded portion to couple the second member to the third member.

13. A surgical system as recited in claim 12, wherein the collet is movable between a first, closed position and a second, open position, the collet being biased to the first, closed position.

14. A surgical system as recited in claim 12, wherein the mating surface is positioned outside of the passageways.

15. A surgical system as recited in claim 12, wherein the reamer end surface is positioned distal to the collet.

16. A surgical system as recited in claim 12, wherein the reamer end surface includes a plurality of teeth.

17. A surgical system as recited in claim 12, further comprising a retaining cap having a threaded outer surface that engages a second inner thread of the second end of the third member, the first member extending through the retaining cap.

18. A surgical system as recited in claim 12, wherein the first end of the fastener includes a spherical shape.

19. A surgical system as recited in claim 12, wherein the collet is configured to snap around the first end of the fastener.

20. A surgical system comprising:
a bone fastener comprising a spherical first end including a socket and a threaded second end configured to penetrate tissue;
a driver member extending along a longitudinal axis between a first end that is disposed within the socket and an opposite second end that includes a mating surface;
a first sleeve defining a first passageway having the driver member disposed therein, the first sleeve extending between a first end and a second end that includes a threaded portion, the first end of the first sleeve comprising a collet that engages the first end of the fastener, the collet comprising a plurality of spaced apart fingers;
a pin that extends through the driver member and into an elongated slot in the first sleeve to prevent the driver member from rotating relative to the first sleeve in opposite directions about the longitudinal axis while allowing the driver member to move axially relative to the first sleeve along the longitudinal axis in opposite directions;
a second sleeve defining a second passageway having the first sleeve disposed therein, the second sleeve extending between a first end that includes a reamer end surface and a second end that includes an inner thread that engages the threaded portion to couple the first sleeve to the second sleeve; and
a retaining cap having a threaded outer surface that engages a second inner thread of the second end of the second sleeve, the driver member extending through the retaining cap,
wherein the collet is movable between a first, closed position and a second, open position, the collet being biased to the first, closed position.

* * * * *